United States Patent [19]

Azuma et al.

[11] Patent Number: 5,034,319

[45] Date of Patent: Jul. 23, 1991

[54] PROCESS FOR PRODUCING L-ARGININE

[75] Inventors: Tomoki Azuma, Hofu; Seiji Aoyagi, Tokyo; Toshihide Nakanishi, Hofu, all of Japan

[73] Assignee: Kyowa Hakko Kogyo Co., Ltd., Tokyo, Japan

[21] Appl. No.: 334,328

[22] Filed: Apr. 7, 1989

[30] Foreign Application Priority Data

Apr. 7, 1988 [JP] Japan .................................. 63-86097

[51] Int. Cl.$^5$ ........................ C12P 13/10; C12N 1/12; C12N 15/00

[52] U.S. Cl. ................................ 435/114; 435/252.1; 435/172.1

[58] Field of Search ............ 435/114, 843, 840, 252.1, 435/172.1

[56] References Cited

U.S. PATENT DOCUMENTS

| | | | |
|---|---|---|---|
| 3,707,441 | 12/1972 | Shiio et al. | 435/115 |
| 3,723,249 | 3/1973 | Kubota et al. | 435/114 |
| 4,346,169 | 8/1982 | Akashi et al. | 435/114 |
| 4,411,991 | 10/1983 | Hirakawa | 435/42 |
| 4,775,623 | 10/1988 | Katsumata et al. | 435/114 |

OTHER PUBLICATIONS

Agricultural & Biological Chemistry, 36, 1675-1684 (1972).

Journal of General and Applied Microbiology 19, 339-352 (1973); 16, 373-391 (1970) (Kubota).

Primary Examiner—Douglas W. Robinson
Assistant Examiner—Irene Marx
Attorney, Agent, or Firm—Antonelli, Terry, Stout & Kraus

[57] ABSTRACT

Disclosed is a process for producing L-arginine, which comprises culturing in a medium a coryneform glutamic acid-producing bacterium having resistance to cysteine or a cysteine analogue and an ability to produce L-arginine, accumulating L-arginine in the culture and recovering the L-arginine therefrom.

6 Claims, No Drawings

PROCESS FOR PRODUCING L-ARGININE

BACKGROUND OF THE INVENTION

The present invention relates to a process for producing L-arginine, which is an amino acid useful as a medicament, food and the like.

Heretofore, L-arginine has been produced by fermentation methods or by extraction from proteins. As the fermentation method, a process using a strain resistant to an arginine analogue [Agricultural & Biological Chemistry, 36, 1675 (1972), Journal of General & Applied Microbiology, 19, 339 (1973), and Japanese Published Examined Patent Application No. 3391/1973]U.S. Pat. No. 3,723,249; a process using a microorganism belonging to the genus Corynebacterium and having resistance to a pyrimidine analogue (Japanese Published Examined Patent Application No. 50479/1982,; and a process using a strain carrying a recombinant DNA comprising a gene involved in the L-arginine biosynthetic pathway and a vector DNA (Japanese Published Unexamined Patent Application No. 66989/1985, U.S. Pat. No. 4,775,623) are known.

Further, known is a process for producing L-lysine by fermentation, which employs a strain of the genus Brevibacterium resistant to S-2-aminoethylcysteine [Journal of General & Applied Microbiology, 16, 373 (1970)].

There has been a demand for a process for producing L-arginine with a higher yield and at a lower cost.

SUMMARY OF THE INVENTION

According to the present invention, L-arginine can be produced by culturing in a medium a coryneform glutamic acid-producing bacterium having resistance to cysteine or a cysteine analogue and an ability to produce L-arginine, accumulating L-arginine in the culture and recovering the L-arginine therefrom.

DETAILED DESCRIPTION OF THE INVENTION

As the microorganism used in the process of the present invention, any coryneform glutamic acid-producing bacterium may be used so long as it has resistance to cysteine or a cysteine analogue and an ability to produce L-arginine.

The coryneform glutamic acid-producing bacterium herein referred to is a microorganism belonging to the genus Corynebacterium or Brevibacterium.

The cysteine analogue referred to herein means such an analogue that when the analogue is added to a minimal agar plate medium and a coryneform glutamic acid-producing bacterium is cultured in the medium, growth of the bacterium is inhibited and this inhibition is released by having the medium contain cysteine. The analogue includes, for example, S-ethylcysteine, S-methylcysteine, S-2-aminoethylcysteine, homocysteine, cysteic acid, homocysteic acid and allylglycine.

As the microorganism belonging to the genus *Corynebacterium* and *Brevibacterium* to be used in the present invention, strains belonging to the species *Corynebacterium glutamicum*, *Corynebacterium acetoacidophilum*, *Corynebacterium lilium*, *Brevibacterium flavum*, *Brevibacterium lactofermentum*, *Brevibacterium divaricatum* and the like are appropriate.

The mutant strains of the present invention are derived from the above-mentioned strains in accordance with the conventional mutagenesis.

The mutant strain can be obtained by endowing an L-arginine-producing strain with resistance to cysteine or a cysteine analogue, or alternatively by endowing a strain already having resistance to cysteine or a cysteine analogue with the ability to produce L-arginine.

As illustrative examples, mention can be made of *Corynebacterium glutamicum* H-7096 (FERM BP-1823) (hereinafter referred to as H-7096 strain), *Corynebacterium acetoacidophilum* H-7092 (FERM BP-1820) (hereinafter referred to as H-7092 strain), *Corynebacterium acetoacidophilum* H-7093 (FERM BP-1821) (hereinafter referred to as H-7093 strain), and *Corynebacterium acetoacidophilum* H-7117 (FERM BP-1822) (hereinafter referred to as H-7117 strain). These strains have been deposited under the Budapest Treaty with the Fermentation Research Institute (FRI), Agency of Industrial Science and Technology, Japan since Mar. 28, 1988.

The methods of obtaining the above-mentioned strains used in the process of the present invention are illustrated below.

(1) Method of obtaining H-7096 strain

*Corynebacterium glutamicum* KY-10671 (FERM P-3616) (D-Ser$^S$, D-Arg$^R$, ArgHx$^R$, 6AU$^R$) (hereinafter referred to as KY-10671 strain) was treated with N-methyl-N'-nitro-N-nitrosoguanidine (250 μg/ml) at 30° C. for 30 minutes. The treated strain was spread on a minimal agar medium [10 g/l glucose, 1 g/l ammonium chloride, 2 g/l urea, 1 g/l KH$_2$PO$_4$, 3 g/l K$_2$HPO$_4$, 0.4 g/l MgCl$_2$.2H$_2$O, 10 mg/l FeSO$_4$.7H$_2$O, 10 mg/l MnSO$_4$.4H$_2$O, 1 mg/l ZnSO$_4$.7H$_2$O, 1 mg/l CuSO$_4$.5H$_2$O, 1 mg/l (NH$_4$)$_6$M$_{07}$O$_{24}$.4H$_2$O, 50 μg/l biotin and 20 g/l agar; pH 7.2] containing S-ethylcysteine at the concentration of 10 mg/ml. Growth of the parent strain is inhibited by S-ethylcysteine at such concentration. Incubation was carried out at 30° C. for 7 to 10 days. Among mutant strains grown, H-7096 (D-Ser$^S$, D-Arg$^R$, ArgHx$^R$, 6AU$^R$, SEC$^R$) was selected as a strain with higher L-arginine productivity.

D-Ser$^S$: D-serine sensitivity, D-Arg$^R$: D-arginine resistance, ArgHx$^R$: arginine hydroxamate resistance, 6AU$^R$: 6-azauracil resistance, SEC$^R$: S-ethylcysteine resistance (2) Method of obtaining H-7092, H-7093 and H-7117 strains H-7092 strain [ArgHx$^R$, 2TA$^R$, 6AU$^R$, (MFA+CBZ Arg)$^R$, SMC$^R$], H-7093 strain [ArgHx$^R$, 2TA$^R$, 6AU$^R$, (MFA+CBZ Arg)$^R$, AEC$^R$] or H-7117 strain [ArgHx$^R$, 2TA$^R$, 6AU$^R$, (MFA+CBZ Arg)$^R$, CYS$^R$] was obtained in the same manner as (1) above, except that *Corynebacterium acetoacidophilum* H-4313 [ArgHx$^R$, 2TA$^R$, 6AU$^R$, (MFA+CBZ Arg)$^R$] (hereinafter referred to as H-4313 strain) was used as the parent strain in place of KY-10671 strain, and that S-methylcysteine, S-2-aminoethylcysteine or cysteine was used in place of S-ethylcysteine.

2TA$^R$: 2-thiazolealanine resistance
(MFA+CBZ Arg)$^R$: N-carbobenzoxyarginine resistance in the presence of monofluoroacetic acid
SMC$^R$: S-methylcysteine resistance
AEC$^R$: S-2-aminoethylcysteine resistance
CYS$^R$: Cysteine resistance Table 1 shows the growth extent of the above-mentioned parent strains and mutant strains when cultured at 30° C. for 24 hours on minimal agar plate media containing cysteine or a cysteine analogue.

TABLE 1

| Chemicals | | Strains | | | | | |
|---|---|---|---|---|---|---|---|
| Type | Concentration (mg/ml) | KY-10671 | H-7096 | H-4313 | H-7092 | H-7093 | H-7117 |
| S-ethyl-cysteine | 0 | ++ | ++ | | | | |
| | 5 | + | ++ | | | | |
| | 10 | − | ++ | | | | |
| S-2-methyl-cysteine | 0 | | | ++ | ++ | | |
| | 5 | | | + | ++ | | |
| | 10 | | | − | ++ | | |
| S-2-amino-ethylcysteine | 0 | | | ++ | | ++ | |
| | 5 | | | − | | ++ | |
| | 10 | | | − | | ++ | |
| Cysteine | 0 | | | ++ | | | ++ |
| | 10 | | | − | | | ++ |
| | 20 | | | − | | | + |

++: Satisfactory growth, +: Moderate growth, −: No growth

For the cultivation of the strains used in the present invention, any culture media commonly employed for the fermentation production of amino acids may be used; namely, synthetic or natural media containing carbon sources, nitrogen sources, inorganic salts and other nutrients that can be assimilated by the strain used.

As the carbon sources, saccharides such as glucose, fructose, sucrose, molasses, starch and starch hydrolyzate; organic acids such as acetic acid, fumaric acid and citric acid; and alcohols such as ethanol, methanol and glycerol can be used.

As the nitrogen sources, ammonia; inorganic ammonium salts such as ammonium chloride, ammonium sulfate, ammonium acetate and ammonium phosphate; organic ammonium salts such as ammonium fumarate; amines such as ethylamine; nitrogen-containing compounds such as urea; and nitrogenous organic substances such as peptone, meat extract, yeast extract, corn steep liquor, casein hydrolyzate, soybean cakes and hydrolyzate thereof, and waste cells used for amino acid and nucleotide fermentation and its digested product thereof can be used.

As the inorganic salts, potassium dihydrogen phosphate, dipotassium hydrogen phosphate, magnesium phosphate, magnesium sulfate, sodium chloride, ferrous sulfate, manganese sulfate, copper sulfate and calcium carbonate can be used.

In addition, if necessary, vitamins such as biotin, thiamine, nicotinic acid and β-alanine and amino acids such as glutamic acid can also be added to the medium.

Culturing is carried out under aerobic conditions by shaking culture, agitation submerged culture or the like at a temperature of 20° to 40° C., preferably 25° to 38° C. The pH of the medium is held within the range of from 5 to 9, preferably around neutrality, by addition of calcium carbonate, an inorganic or organic acid, an alkali solution, ammonia or a pH buffer solution.

Usually, after culturing for one to 7 days under these conditions, L-arginine can be accumulated in the culture.

After the completion of culturing the L-arginine thus accumulated can be isolated from the culture by removing precipitates such as the microbial cells from the culture through filtration or centrifugation, and treating the filtrate or supernatant by a proper combination of known techniques such as treatment with ion-exchange resin, concentration, salting-out and isoelectric precipitation.

The present invention is illustrated by the following representative Examples.

EXAMPLE 1

H-7096 and KY-10671 strains were each cultured in 6 ml of a seed medium comprising 20 g/l glucose, 10 g/l peptone, 10 g/l yeast extract and 5 g/l NaCl (pH 7.2) at 30° C. for 24 hours. Each of the seed cultures thus obtained (2 ml) was inoculated to 20 ml of a production medium having the following composition in a 300 ml-conical flask, and shaking culture was carried out at 30° C. for 72 hours.

The amounts of L-arginine formed in the culture were 24.5 mg/ml and 22.0 mg/ml, respectively.

(Composition of the production medium)
150 g/l cane molasses (as glucose), 30 g/l ammonium sulfate, 3 g/l urea, 0.5 g/l $KH_2PO_4$, 0.5 g/l $K_2HPO_4$, 0.25 g/l $MgSO_4.2H_2O$, 30 g/l $CaCO_3$ (pH 7.2)

The fermentation broth of H-7096 strain was subjected to centrifugation, and 1 l of the supernatant was passed through a column packed with a strongly acidic cation-exchange resin [Dowex 50×8 (Na form); Dow Chemical Co.], adsorbed L-arginine was eluted with aqueous ammonia, and the eluent was purified and concentrated, giving 19.6 g of L-arginine as crystals.

EXAMPLE 2

H-4313, H-7092, H-7093 and H-7117 strains were each cultured in 6 ml of a seed medium containing 50 g/l glucose, 10 g/l peptone, 10 g/l yeast extract, 5 g/l ammonium sulfate, 5 g/l $KH_2PO_4$, 0.5 g/l $MgSO_4.2H_2O$, 50 µg/ml biotin and 5 g/l NaCl (pH 7.2) at 30° C. for 24 hours. Each of the seed cultures thus obtained (2 ml) was inoculated to 20 ml of a production medium having the following composition in a 300 ml-conical flask, and shaking culture was carried out at 30° C. for 72 hours.

(Composition of the production medium)
80 g/l cane molasses (as glucose), 0.5 g/l $KH_2PO_4$, 0.5 g/l $K_2HPO_4$, 45 g/l ammonium sulfate, 2 g/l urea, 30 g/l $CaCO_3$ (pH 7.2)

The amounts of L-arginine formed in the culture are shown in Table 2.

TABLE 2

| Strain | Amt. of L-arginine formed (mg/ml) |
|---|---|
| H-7092 | 24.0 |
| H-7093 | 23.5 |
| H-7117 | 23.2 |

TABLE 2-continued

| Strain | Amt. of L-arginine formed (mg/ml) |
|---|---|
| H-4313 | 21.0 |

EXAMPLE 3

H-7092 strain was cultured in 250 ml of a seed medium (pH 7.2) comprising 50 g/l glucose, 10 g/l peptone, 10 g/l yeast extract, 5 g/l corn steep liquor, 3 g/l urea, 2.5 g/l NaCl and 50 μg/l d-biotin on a rotary shaker at 30° C. for 24 hours. The obtained seed culture was inoculated to 1.6 l of a production medium having the following composition in a 5 l-jar fermentor, and shaking culture was carried out at 600 rpm and an aeration rate of 3 l/min at 30° C. for 72 hours. The pH was maintained at 6.6 using 10N $NH_4OH$. When the sugar initially present had been consumed, 1.4 l of a feeding medium having the following composition was added. After completion of the culturing, 66 g/l of L-arginine was accumulated. Then, 52.8 g/l of L-arginine was obtained as crystals from the culture broth by the same method as in Example 1.

(Composition of the production medium)
  70 g/l cane molasses (as glucose), 5 g/l $KH_2PO_4$, 38 g/l $(NH_4)_2SO_4$, 5 g/l $MgSO_4.7H_2O$, 10 mg/l $FeSO_4.7H_2O$ and 100 μg/l thiamine hydrochloride (pH 7.2)

(Composition of the feeding medium)
  400 g/l cane molasses (as glucose) and 40 g/l $(NH_4)_2SO_4$

What is claimed is:

1. A process for producing L-arginine which comprises culturing in a medium a microorganism selected from the group consisting of *Corynebacterium gultamicum* H-7096 (FERM BP-1823) having resistance to S-ethylcystein, *Corynebacterium acetoacidophilum* H-7092 (FERM BP-1820) having resistance to S-methylcysteine and *Corynebacterium acetoacidophilum* H-7093 (FERM BP-1821) having resistance to a S-2-aminoethylcysteine, accumulating L-arginine in the culture and recovering the L-arginine therefrom.

2. A process for producing L-arginine which comprises culturing in a medium *Corynebacterium acetoacidophilum* H-7117 (FERM BP-1822) being capable of growing in a medium containing cysteine in a concentration of 10 mg/ml or more and having an ability to produce L-arginine, accumulating L-arginine in the culture and recovering the L-arginine therefrom.

3. A biologically pure culture of *Corynebacterium glutamicum* H-7096 (FERM BP-1823).

4. A biologically pure culture of *Corynebacterium acetoacidophilum* H-7092 (FERM BP-1820).

5. A biologically pure culture of *Corynebacterium acetoacidophilum* H-7093 (FERM BP-1821).

6. A biologically pure culture of *Corynebacterium acetoacidophilum* H-7117 (FERM BP-1822).

* * * * *